United States Patent
Kimball et al.

(10) Patent No.: US 12,280,065 B2
(45) Date of Patent: Apr. 22, 2025

(54) PHARMACEUTICAL COMPOUNDS AND THERAPEUTIC METHODS

(71) Applicant: RUTGERS, THE STATE UNIVERSITY OF NEW JERSEY, New Brunswick, NJ (US)

(72) Inventors: Spencer David Kimball, New Brunswick, NJ (US); Darren R. Carpizo, New Brunswick, NJ (US); John A. Gilleran, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 785 days.

(21) Appl. No.: 17/605,750

(22) PCT Filed: Apr. 22, 2020

(86) PCT No.: PCT/US2020/029382
§ 371 (c)(1),
(2) Date: Oct. 22, 2021

(87) PCT Pub. No.: WO2020/219589
PCT Pub. Date: Oct. 29, 2020

(65) Prior Publication Data
US 2022/0096492 A1    Mar. 31, 2022

Related U.S. Application Data

(60) Provisional application No. 62/837,717, filed on Apr. 23, 2019.

(51) Int. Cl.
| | |
|---|---|
| *A61K 31/555* | (2006.01) |
| *A61K 31/282* | (2006.01) |
| *A61K 31/337* | (2006.01) |
| *A61K 31/395* | (2006.01) |
| *A61K 31/437* | (2006.01) |
| *A61K 31/4745* | (2006.01) |
| *A61K 31/475* | (2006.01) |
| *A61K 31/506* | (2006.01) |
| *A61K 31/704* | (2006.01) |
| *A61K 31/7068* | (2006.01) |
| *A61K 38/14* | (2006.01) |
| *A61P 35/00* | (2006.01) |
| *C07F 3/06* | (2006.01) |

(52) U.S. Cl.
CPC .......... *A61K 31/555* (2013.01); *A61K 31/282* (2013.01); *A61K 31/337* (2013.01); *A61K 31/437* (2013.01); *A61K 31/4745* (2013.01); *A61K 31/475* (2013.01); *A61K 31/506* (2013.01); *A61K 31/5545* (2017.08); *A61K 31/704* (2013.01); *A61K 31/7068* (2013.01); *A61K 38/14* (2013.01); *A61P 35/00* (2018.01); *C07F 3/06* (2013.01)

(58) Field of Classification Search
None
See application file for complete search history.

(56) References Cited

U.S. PATENT DOCUMENTS

| | | | |
|---|---|---|---|
| 4,657,903 | A | 4/1987 | Scovill et al. |
| 4,665,173 | A | 5/1987 | Klayman et al. |
| 4,777,166 | A | 10/1988 | Smith et al. |
| 7,112,680 | B2 | 9/2006 | Hofmann et al. |
| 10,221,133 | B2 | 3/2019 | Augeri et al. |
| 10,604,480 | B2 | 3/2020 | Augeri et al. |
| 10,604,481 | B2 | 3/2020 | Augeri et al. |
| 10,729,671 | B2 | 8/2020 | Augeri et al. |
| 10,828,288 | B2 | 11/2020 | Augeri et al. |
| 2008/0118576 | A1 | 5/2008 | Theodorescu et al. |
| 2013/0345164 | A1 | 12/2013 | Vazquez et al. |
| 2014/0142266 | A1 | 5/2014 | Sakamoto et al. |
| 2018/0000772 | A1 | 1/2018 | Augeri et al. |
| 2018/0000806 | A1 | 1/2018 | Augeri et al. |
| 2018/0002279 | A1 | 1/2018 | Augeri et al. |
| 2018/0002280 | A1 | 1/2018 | Augeri et al. |
| 2022/0185827 | A1 | 6/2022 | Kimball et al. |

FOREIGN PATENT DOCUMENTS

| | | | |
|---|---|---|---|
| WO | 2001094340 | A1 | 12/2001 |
| WO | 2006019955 | A2 | 2/2006 |

(Continued)

OTHER PUBLICATIONS

Loh, S. N., Follow the Mutations: Toward Class-Specific, Small-Molecule Reactivation of p53. Biomolecules, 2020, 10, 303, p. 1-14.*

(Continued)

*Primary Examiner* — Po-Chih Chen
(74) *Attorney, Agent, or Firm* — Viksnins Harris Padys Malen LLP

(57) ABSTRACT

The invention provides a complex comprising Zn2+ and a compound of formula (I): or a deuterated analog thereof, or an ion or poly-ion thereof, or a salt thereof that is useful for treating cancer, as well as compositions and kits comprising such complexes.

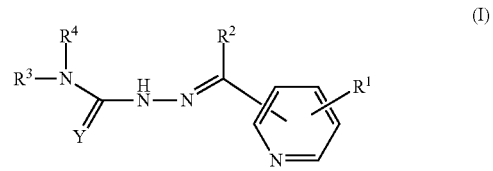

(I)

19 Claims, 2 Drawing Sheets

(56) References Cited

FOREIGN PATENT DOCUMENTS

| WO | 2006101740 A2 | 9/2006 |
| --- | --- | --- |
| WO | 2007035489 A2 | 3/2007 |
| WO | 2009039553 A1 | 4/2009 |
| WO | 2012175962 A1 | 12/2012 |
| WO | 2015021456 A1 | 2/2015 |
| WO | 2016123242 A1 | 8/2016 |
| WO | 2016123246 A1 | 8/2016 |
| WO | 2016123250 A1 | 8/2016 |
| WO | 2016123253 A1 | 8/2016 |
| WO | 2020219587 A1 | 10/2020 |

OTHER PUBLICATIONS

Agrawal, K, et al., "Potential antitumor agents. 13. 4-Methyl-5-amino-1-formylisoquinoline thiosemicarbazone", Journal of Medicinal Chemistry 19(7), 970-972 (1976).

Antonini, I, et al., "Elucidation of the structure of the antineoplastic agents, 2-formylpyridine and 1-formylisoquinoline thiosemicarbazones", Journal of Medicinal Chemistry 20(3), 447-449 (1977).

Bellitto, C, et al., "Conformational Studies of Some Potentially Bidentate Thiosemicarba-zones and Related Complexes of Zinc(II)", J.C.S. Dalton 68570(21), 758-762 (1976).

Bermejo, E, et al., "Complexes of Grup 12 Metals with 2-Acetylpyridine 4N-Dimethyl-thiosemiearbazone and with 2-Acetyipyridine-N-oxide 4N-Dimethyl-thiosemiearbazone: Synthesis, Structure and Antifungal Activity", Zeitschrift fuer Naturforschung, B: Chemical Sciences 54(6), 777-787 (1999).

Bjelogrlic, S, et al., "Synthesis, structure and characterization of novel Cd(II) and Zn(II) complexes with the condensation product of 2-formylpyridine and selenosemicarbazide Antiproliferative activity of the synthesized complexes and related selenosemicarbazone complexes", Journal of Inorganic Biochemistry 104, 673-682 (2010).

Blanden, A, et al., "Synthetic Metallochaperone ZMC1 Rescues Mutant p53 Conformation by Transporting Zinc into Cells as an Ionophore", Mol Pharmacol 87, 825-831 (2015).

Chhabra, N, et al., "A review of drug isomerism and its significance", Int J Appl Basic Med Res 3(1), 16-18 (2013).

Chun-Ying, D, et al., "Synthesis, Crystal Structure and Nonlinear Optical Properties of Thiosemicarbazone Zinc Complex", J Coord Chem 47, 433-439 (1999).

Easmon, J, et al., "2-benzoxazolyl and 2-benzimidazolyl hydrazones derived from 2-acetylpyridine: a novel class of antitumor agents", Int J Cancer 94, 89-96 (2001).

Fasmon, J, et al., "Synthesis, Structure-Activity Relationships, and Antitumor Studies of 2-Benzoxazolyl Hydrazones Derived from Alpha-(N)-acyl Heteroaromatics", J Med Chem 49, 6343-6350 (2006).

Easmon, J, et al., "Thiazolyl and benzothiazolyl hydrazones derived from α-(N)-acetylpyridines and diazines: synthesis, antiproliferative activity and CoMFA studies", Eur J Med Chem 32, 397-408 (1997).

File Caplus, "Preparation and characterization of vanillin thiosemicarbazone complexes with cobalt(II), nickel(II), copper(II), zinc(II), cadmium(II), and mercury(II)", STN CA Caesar Accession No. 1170, 2 pages (1984).

File Caplus, "Synthesis and crystal structure of zinc(II) complex [Zn(25-MBTSC)212]", STN CA Caesar Accession No. 1162, 1 page (2013).

File Caplus, "Synthesis and structure of 1.5Zn(phen)3·L·cntdot..3N03 supramolecule (phen = o-phenanthroline, L = 4-aminoacetophenone thiosemicarbazone", STN CA Caesar Accession No. 1176, 2 pages (2008).

Gudasi, K, et al., "Synthesis and spectral investigation of some transition metal complexes containing pentadentate macroacyclic NNNNN-donor Schiff base ligands", Transition Metal Chemistry 30, 726-732 (2005).

Hall, I, et al., "Investigations on the Mechanism of Action of the Novel Antitumor Agents 2-Benzothiazolyl, 2-Benzoxazolyl, and 2-Benzimidazolyl Hydrazones Derived from 2-Acetylpyridine", Arch Pharm Pharm Med Chem 332 (4), 115-123 (1999).

Heit, et al., "Substituted Hydrazones as Tridentate Chelating Agents", Analytica Chimica Acta 32, 448-455 (1965).

Huang, H, et al., "A Series of α-Heterocyclic Carboxaldehyde Thiosemicarbazones Inhibit Topoisomerase IIα Catalytic Activity", Journal of Medicinal Chemistry 53, 3048-3064 (2010).

Huang, Y, et al., "Correlating gene expression with chemical scaffolds of cytotoxic agents: ellipticines as substrates and inhibitors of MDR1", Pharmacogenomics Journal 5, 112-125 (2005).

Ibrahim, A, et al., "Indole-7-carbaldehyde thiosemicarbazone as a flexidentate ligand toward ZnII, CdII, PdII and PtII ions: cytotoxic and apoptosis-inducing properties of the PtII complex", Dalton Trans 43, 3860-3860 (2014).

Kalinowski, D, et al., "Design, Synthesis, and Characterization of Novel Iron Chelators: Structure-Activity Relationships of the 2-Benzoylpyridine Thiosemicarbazone Series and Their 3-Nitrobenzoyl Analogues as Potent Antitumor Agents", Journal of Medicinal Chemistry 50(15), 3716-3729 (2007).

Khalaji, A, et al., "Synthesis and Characterization of Zinc(II) Complexes with 3,4-Dimethoxybenzaldehyde Thiosemicarbazone: The Crystal Structure of [Zn(34-MBTSC) 2 CI 2 ]", Phosphorus, Sulfur, and Silicon 188, 1119-1126 (2013).

Khaled, S, et al., "Synthesis and Spectroscopic Characterization of Some NOvel Polypyridine and Phenanthroline Complexes of Mn(II), Fe(II), Co(II) and Zn(II) Incorporating a Bidentate Benzothiazolyl Hydrazone Ligand", Chem Sci Trans 2(4), 1222-1231 (2013).

Kodela, R, et al., "Positional Isomers of Aspirin are Equally Potent in Inhibiting Colon Cancer Cell Growth: Differences in Mode of Cyclooxygenase Inhibition", J Pharmacol Exp Ther 346, 85-94 (2013).

Kovala-Demertzi, D, et al., "Zinc(II) complexes derived from pyridine-2-carbaldehyde thiosemicarbazone and (1E)-1-pyridin-2-ylethan-1-one thiosemicarbazone. Synthesis, crystal structures and antiproliferative activity of zinc(II) complexes", Journal of Inorganic Biochemistry 100, 1558-1567 (2006).

Mohan, M, et al., "Synthesis, Characterization, and Antitumor Properties of some Metal Complexes of 2,6-Diacetylpyridine Bis(N4-azacyclic Thiosemicarbazone)", Journal of Inorganic Biochemistry 34, 41-54 (1988).

Moorthy, N, et al., "QSAR analysis of 2-benzoxazolyl hydrazone derivatives for anticancer activity and its possible target prediction", Med Chem Res 21, 133-144 (2012).

Mrozek-Wilczkiewicz, A, et al., "Iron Chelators in Photodynamic Therapy Revisited: Synergistic Effect by Novel Highly Active Thiosemicarbazones", ACS Medicinal Chemistry Letters 5(4), 336-339 (2014).

Odashima, T, et al., "Determination of Microamounts of Iron by Extraction-Spectrophotometry with 2-Acetylpyridine-2-benzothiazolylhydrazone and Its Sensitization by Employing an Analog Derivative Technique", Microchemical Journal 33, 138-146 (1986).

Patani, George A., et al., "Bioisosterism: A Rational Approach in Drug Design", Chem Rev 96, 3147-3176 (1996).

Patent Cooperation Treaty, International Search Report and Written Opinion for PCT/US2020/029382, 10 pages, dated Sep. 8, 2020.

Priyadharsini, R, et al., "Docking, synthesis, characterization and evaluation of novel cdk2 inhibitors: benzothiazole derivatives", International Journal of Pharmacy and Pharmaceutical Sciences 4(3), 574-585 (2012).

PubChem, "[(Z)-(5-Amino-4-morpholin-4-ylisoquinolin-1-yl)methylideneamino]thiourea", PubChem CID: 44355883, 8 pages, (Nov. 19, 2009).

Rao, P, et al., "Synthesis and Spectroscopic Studies on a Dibasic Pent Dentate Ligand", Inorganic Chemistry 1 (3), 47-52 (2006).

Ren, P, et al., "A new approach to suppress nonlinearity-transparency trade-off through coordination chemistry: syntheses and spectroscopic study on second-order nonlinear optical properties of a series of square-pyramidal zinc (II) complexes", Spectrochimica Acta Part A 59, 1095-1101 (2003).

Richardson, D, et al., "Dipyridyl Thiosemicarbazone Chelators with Potent and Selective Antitumor Activity Form Iron Complexes with Redox Activity", J Med Chem 49, 6510-6521 (2006).

(56) References Cited

OTHER PUBLICATIONS

Ruangpornvisuti, V, et al., "A DFT investigation of conformational geometries and interconversion equilibria of phenylthiosemicarbazone and its complexation with zinc", J Mol Model 10, 418-426 (2004).

Singh, K, et al., "Stereochemistry and Its Role in Drug Design", IJPSR 5(11), 4644-4659 (2014).

Sleebs, B, et al., "Discovery of Potent and Selective Benzothiazole Hydrazone Inhibitors of Bcl-XL", J Med Chem 56, 5514-5540 (2013).

STN Record, Accession No. 1975:461709, JP49126728, 1 page (1975).

Tian, Y, et al., "Structural characterization and second-order nonlinear optical properties of zinc halide thiosemicarbazone complexes", Polyhedron 21, 1217-1222 (2002).

Todorovic, T., et al., "Synthesis and characterization of Zn(II) and Cd(II) complexes with 2,6-diacetylpyridine-bis (selenosemicarbazone). Crystal structure of a Ni(II) complex with a modified 2,6-diacetylpyridine-bis (selenosemicarbazone)", Inorganic Chemistry Communications 9, 862-865 (2006).

Vartale, S, et al., "Synthesis and Antimicrobial Activity of 6/7/8-Substituted-1-[ARYL/6' Substituted-2'-Benzothiazolyl]-Pyrazolo [4,5-b] Quinolines", Indian Journal of Heterocyclic Chemistry 16, 163-166 (2006).

Webster, D, et al., "Synthesis and characterization of novel pentagonal bipyramidal complexes of iron(II), cobalt(II), and zinc(II)", Journal of American Chemical Society 95(19), 6505-6506 (1973).

Yu, X, et al., "Allele-Specific p53 Mutant Reactivation", Cancer Cell 21, 614-625 (2012).

Yu, X, et al., "Small molecule restoration of wildtype structure and function of mutant p53 using a novel zinc-metallochaperone based mechanism", Oncotarget 5(19), 8879-8892 (2014).

\* cited by examiner

PHARMACEUTICAL COMPOUNDS AND THERAPEUTIC METHODS

PRIORITY OF INVENTION

This application claims priority to U.S. Provisional Application No. 62/837,717, filed 23 Apr. 2019. The entire content of this application is incorporated herein by reference.

STATEMENT REGARDING FEDERALLY SPONSORED RESEARCH

This invention was made with government support under CA200800 and CA172676 awarded by the National Institutes of Health. The Government has certain rights in this invention.

BACKGROUND OF THE INVENTION

TP53 is the most commonly mutated gene in human cancer for which no effective targeted anti-cancer drug exists. The majority of TP53 mutations (>70%) are missense mutations that generate a defective protein that is generally found at high levels in cancer cells due to loss of MDM2 negative feedback. Restoring the function of p53 in mouse models of cancer is highly therapeutic. Reactivating mutant p53 using small molecules has been highly sought after, yet remains an elusive goal in the development of cancer therapeutics. Currently there is a need for additional cancer therapeutics. In particular, there is a need for cancer therapeutics with acceptable solubility that can reactivate mutant p53.

SUMMARY OF THE INVENTION

This invention provides novel complexes, kits, and methods directed toward refolding TP53 mutant proteins into their wild-type conformations by treatment with zinc(II) metallochaperone complexes.

More specifically, one aspect of the present invention provides a complex of the invention, which is a complex comprising $Zn^{2+}$ and a compound of formula (I):

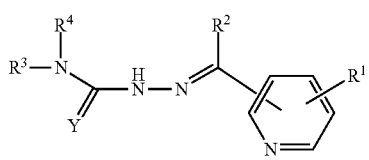

(I)

or an ion or poly-ion thereof, or a salt of said complex, wherein:

$R^1$ is morpholinomethyl, 2-morpholinoethyl, or $(C_1-C_6)$ alkyl that is substituted with $(C_1-C_6)$alkoxy that is substituted with one or more groups independently selected from $(C_1-C_6)$alkoxy, halo, cyano, $(C_3-C_6)$cycloalkyl, $(C_2-C_6)$alkanoyloxy, $(C_2-C_6)$alkoxycarbonyl, and $-N(R^a)_2$;

$R^2$ is selected from the group consisting of H, phenyl, heteroaryl, $(C_1-C_6)$alkyl, $(C_2-C_6)$alkenyl, $(C_2-C_6)$alkynyl, and $(C_3-C_6)$cycloalkyl, wherein any phenyl, heteroaryl, $(C_1-C_6)$alkyl, $(C_2-C_6)$alkenyl, $(C_2-C_6)$alkynyl, $(C_3-C_6)$cycloalkyl and $C_4-C_6$ heterocycloalkyl, is optionally substituted with one or more groups independently selected from halo, $-N(R^b)_2$, $(C_3-C_6)$cycloalkyl, $(C_1-C_6)$alkoxy, $(C_2-C_6)$alkanoyloxy, $(C_2-C_6)$alkoxycarbonyl, $(C_2-C_6)$ alkylaminocarbonyl, and $(C_2-C_6)$alkanoylamino:

$R^3$ and $R^4$ are each independently selected from H, $(C_1-C_6)$alkyl, piperidinyl, or piperazinyl, which piperidinyl or piperazinyl is optionally substituted with pyridyl; or $R^3$ and each $R^4$ taken together with the nitrogen to which they are attached form a 3, 4, 5, 6, 7, 8, or 9 membered ring that is optionally substituted with one or more groups independently selected from the group consisting of halo;

Y is S, O, or Se;

each $R^a$ is independently selected from the group consisting of H, $(C_1-C_6)$alkyl, $(C_3-C_6)$alkenyl, $(C_3-C_6)$alkynyl, $(C_3-C_6)$cycloalkyl, $(C_1-C_6)$alkanoyl, $(C_1-C_6)$alkylaminocarbonyl and $(C_1-C_6)$alkoxycarbonyl, wherein any $(C_1-C_6)$alkyl, $(C_3-C_6)$alkenyl, $(C_3-C_6)$alkynyl, $(C_3-C_6)$cycloalkyl, $(C_1-C_6)$alkanoyl, and $(C_1-C_6)$alkoxycarbonyl, $(C_1-C_6)$alkylaminocarbonyl, and $(C_2-C_6)$alkanoylamino is optionally substituted with one or more groups independently selected from halo, $(C_3-C_6)$cycloalkyl, and $(C_1-C_6)$alkoxy; or two $R^a$ taken together with the nitrogen to which they are attached form a ring, e.g., azetidino, pyrrolidino, piperidino, or morpholino; and each $R^b$ is independently selected from the group consisting of H, $(C_1-C_6)$alkyl, $(C_3-C_6)$alkenyl, $(C_3-C_6)$alkynyl, $(C_3-C_6)$cycloalkyl, $(C_1-C_6)$alkanoyl, $(C_1-C_6)$alkylaminocarbonyl and $(C_1-C_6)$alkoxycarbonyl, wherein any $(C_1-C_6)$alkyl, $(C_3-C_6)$alkenyl, $(C_3-C_6)$alkynyl, $(C_3-C_6)$cycloalkyl, $(C_1-C_6)$alkanoyl, and $(C_1-C_6)$alkoxycarbonyl, $(C_1-C_6)$alkylaminocarbonyl, and $(C_2-C_6)$alkanoylamino is optionally substituted with one or more groups independently selected from halo, $(C_3-C_6)$cycloalkyl, and $(C_1-C_6)$alkoxy; or two $R^a$ taken together with the nitrogen to which they are attached form a ring, e.g., azetidino, pyrrolidino, piperidino, or morpholino.

Another aspect of the present invention provides a salt (e.g. a pharmaceutically acceptable salt) of a complex comprising $Zn^{2+}$ and a compound of formula (I) or an ion or poly-ion thereof.

Another aspect of the present invention provides a method of inhibiting cancer cell growth comprising administering to a human afflicted with cancer, an amount of a complex of the invention having a $Zn^{2+}$ ion.

Another aspect of the present invention provides a method comprising combining $Zn^{2+}$ ions and a monomer of formula (I) in a ratio of 2:1 (monomer:zinc) to form a neutral complex, or forming a pharmaceutically acceptable salt of such neutral complex; and diffusing the complex across a plasma membrane of a cell under conditions where the $Zn^{2+}$ ion will bind to a native ligation site of a mutant p53 inside the cell.

Another aspect of the present invention provides a pharmaceutical composition comprising, in a pharmaceutically acceptable carrier, a compound or complex to release zinc to p53.

Another aspect of the present invention provides a method of inhibiting cancer cell growth, comprising administering to an animal (e.g. a human), an effective amount of a compound or complex as described herein.

Another aspect of the present invention provides a method of inhibiting cancer cell growth, comprising administering to a human in need thereof, an effective amount of a complex as described herein and further comprising administering to the human a zinc supplement.

Another aspect of the present invention provides a method of inhibiting cancer cell growth comprising administering to a human afflicted with cancer, an amount of a neutral complex of the invention having a $Zn^{2+}$ ion or a pharmaceutically acceptable salt of such a neutral complex, effective to inhibit growth of cancer cells in the human.

Another aspect of the present invention provides a method comprising: binding a $Zn^{2+}$ ion to a monomer of formula (I) in a ratio of 2:1 (monomer:zinc) to form a complex outside a cell; diffusing the complex or a pharmaceutically acceptable salt thereof, including the $Zn^{2+}$ ion across a plasma membrane of the cell; and binding the $Zn^{2+}$ ion to a native ligation site of a mutant p53 inside the cell.

The invention further includes methods of preparing, methods of separating, and methods of purifying of the complexes described herein.

Additional advantages and novel features of this invention shall be set forth in part in the description that follows, and in part will become apparent to those skilled in the art upon examination of the following specification, or may be learned by the practice of the invention.

The advantages of the invention may be realized and attained by means of the instrumentalities, combinations, compositions, and methods particularly pointed out in the appended claims.

DESCRIPTION OF THE INVENTION

Figure 1:
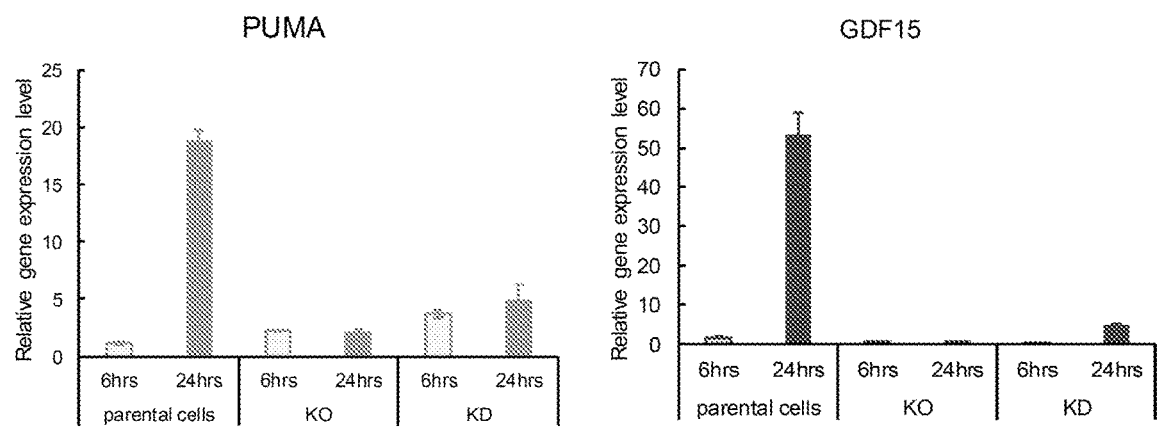
FIG. 1 shows data from Example 7.

The following definitions are used, unless otherwise described: halo is fluoro, chloro, bromo, or iodo. Alkyl, alkoxy, etc. denote both straight and branched groups: but reference to an individual radical such as propyl embraces only the straight chain radical, a branched chain isomer such as isopropyl being specifically referred to.

The term "butyl" as used herein refers to a four-carbon alkyl radical, substituent, or molecular fragment having the chemical formula —$C_4H_9$.

The term "cyclopropyl" as used herein refers to a radical, substituent, or molecular fragment having a chemical structure derived from cyclopropane and having the chemical formula $C_3H_5$.

The term "ethyl" as used herein refers to an alkyl substituent, radical, or molecular fragment having the chemical formula —$C_2H_5$.

The term "isopropyl" as used herein refers to a propyl with a group attached to the secondary carbon.

The term "methyl" as used herein refers to an alkyl derived from methane and containing one carbon atom bonded to three hydrogen atoms and having the chemical formula —$CH_3$.

The term "propyl" as used herein refers to a linear three-carbon alkyl substituent, molecular fragment, or radical having the chemical formula —$C_3H_7$.

The term "phenyl" refers to a cyclic group of atoms, radical, substituent, or molecular fragment having the chemical formula —$C_6H_5$.

Deuterated

The term "deuterated" means enriched in deuterium above its natural abundance at one or more positions of a compound. When a particular position, for example, a carbon atom, is deuterated, it is understood that the abundance of deuterium at that position is substantially greater than the natural abundance of deuterium, which is 0.015%. A deuterated position typically has a minimum isotopic enrichment factor of at least 3000 (45% deuterium incorporation).

The term "isotopic enrichment factor" as used herein means the ratio between the isotopic abundance and the natural abundance of a specified isotope. In certain embodiments, a compound has an isotopic enrichment factor of at least 3500 (52.5% deuterium incorporation) at a given deuterated atom, at least 4000 (60% deuterium incorporation), at least 4500 (67.5% deuterium incorporation), at least 5000 (75% deuterium incorporation), at least 5500 (82.5% deuterium incorporation), at least 6000 (90° % deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). In some embodiments, 100% deuterium incorporation is achieved.

It is to be understood that a deuterated compound contains one or more deuterium atoms. For example, a deuterated compound may contain just one deuterium. In some embodiments, a deuterated compound contains just two deuteriums. In some embodiments, a deuterated compound contains only three deuteriums. In some embodiments, a deuterated compound contains four deuteriums. In some embodiments, a deuterated compound contains 1, 2, 3, or 4 deuteriums, or any range derivable therein.

Deuterium can be incorporated into a compound of formula (I) using a variety of known reagents and synthetic techniques. For example, deuterium can be incorporated into a compound of formula (I) using $LiAlD_4$. It can also be incorporated into a compound of formula (I) such as through reduction, catalytic hydrogenation or isotopic exchange using appropriate deuterated reagents such as deuterides, $D_2$ and $D_2O$.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

It is further understood by those skilled in the art that compounds of the invention which contain either basic or acidic functionality may be prepared, purified, and administered in the form of pharmaceutically acceptable salts.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_1-C_6)$cycloalkyl can be cyclopropyl, cyclobutyl, cyclopentyl, or cyclohexyl; $(C_1-C_6)$alkoxy can be methoxy, ethoxy, propoxy, isopropoxy, butoxy, iso-butoxy, sec-butoxy, pentoxy, 3-pentoxy, or hexyloxy; and $(C_3-C_6)$cycloalkoxy can be cyclopropyloxy, cyclobutyloxy, cyclopentyloxy, or cyclohexyloxy.

In one specific embodiment, the compound of formula (I) is a compound of formula (Ia):

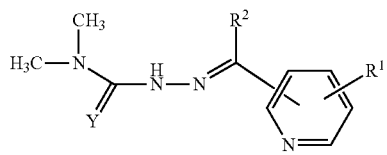

or an ion or poly-ion thereof.

In one specific embodiment, the compound of formula (I) is a compound of formula (Ib):

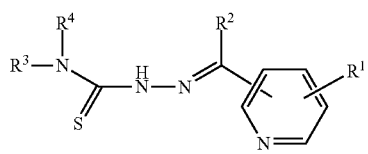

or an ion or poly-ion thereof.

In one specific embodiment, the compound of formula (I) is a compound of formula (Ic):

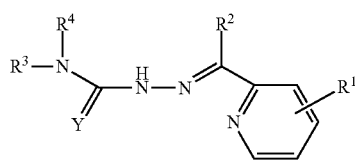

or an ion or poly-ion thereof.

In one specific embodiment, the compound of formula (I) is a compound of formula (Id):

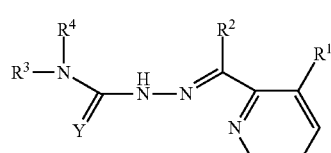

or an ion or poly-ion thereof.

In one specific embodiment, the compound of formula (I) is a compound of formula (Ie):

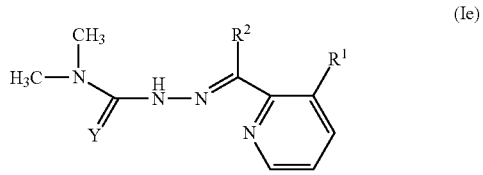

or an ion or poly-ion thereof.

In one specific embodiment, the compound of formula (I) is a compound of formula (If):

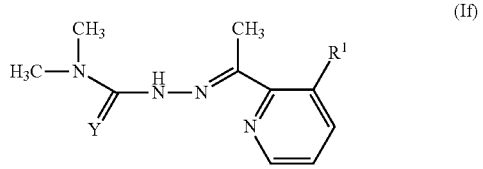

or an ion or poly-ion thereof.

In one specific embodiment, the compound of formula (I) is a compound of formula (Ig):

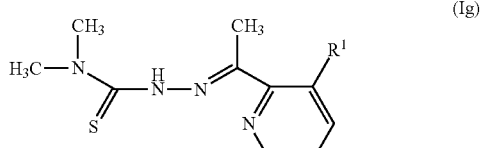

or an ion or poly-ion thereof.

In general, a zinc complex of the invention can be prepared as illustrated in the following scheme.

General Synthesis of 2:1 Zinc Complexes

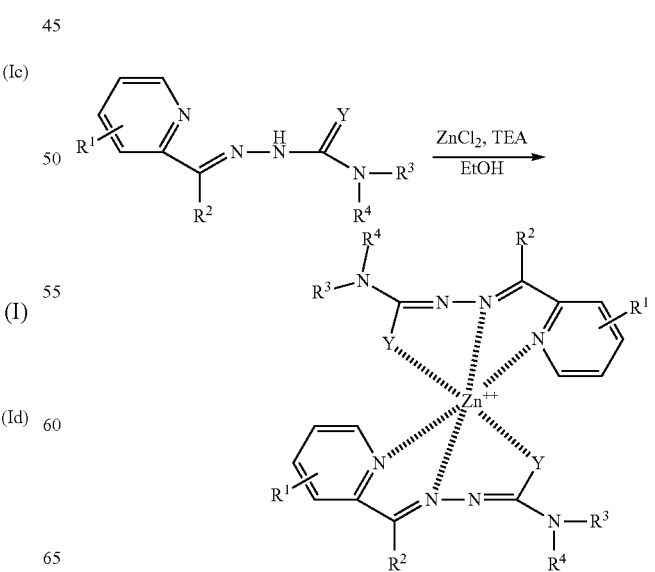

The invention will now be illustrated by the following non-limiting Examples.

EXAMPLES

Example 1 Synthesis of Zn[(E)-N,N-dimethyl-2-(1-(3-(morpholinomethyl)pyridin-2-yl)ethylidene)hydrazine-1-carbothioamide]$_2$ (ZN-7)

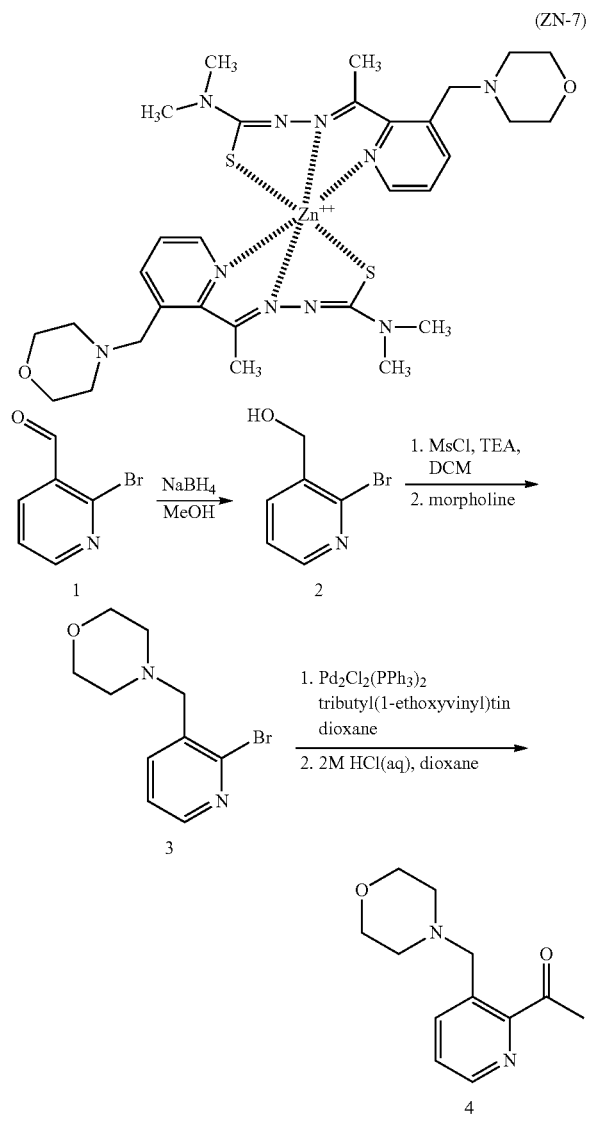

a. Preparation of (2-bromopyridin-3-yl)methanol (2)

2-bromonicotinaldehyde (1) (10 g, 53.8 mmol, 1 eq) was dissolved in 100 ml MeOH and cooled to 0° C. Sodium borohydride (2.04 g, 53.8 mmol, 1 eq) was added, and the reaction was allowed to slowly warm to room temperature. After 1 hour, the reaction was determined to be complete by TLC and concentrated under reduced pressure. The residue was partitioned in DCM and ammonium chloride (dilute, aq). The aqueous was extracted 2×DCM and the combined organic was washed 1× brine, dried over sodium sulfate, filtered and concentrated to afford (2-bromopyridin-3-yl)methanol (2) (9.3 g, 1000% purity by LC/MS) as a white solid. MS: 211.00 [M+H]$^+$.

b. Preparation of 4-((2-bromopyridin-3-yl)methyl)morpholine (3)

To a solution of (2-bromopyridin-3-yl)methanol (2) (1 g, 4.65 mmol, 1 eq) in 40 ml DCM was added sequentially triethylamine (973 uL, 6.98 mmol, 1.5 eq) and methanesulfonyl chloride (360 uL, 4.65 mmol, 1 eq). The reaction was determined complete by TLC after stirring for 20 min at room temperature. MS: 265.44, 267.45 [M+H]$^+$. To this solution of crude mesylate was added morpholine (1.21 ml, 14.0 mmol, 3 eq). After stirring for 1 hour at reflux, the reaction was partitioned in DCM and water. The organic was washed 1× water, 1× brine, dried over sodium sulfate, filtered and concentrated. Purification by column chromatography (25%→50% EtOAc/Hex) afforded 4-((2-bromopyridin-3-yl)methyl)morpholine (3) (quantitative, 95% purity by LC/MS) as a pale yellow oil. MS: 256.85, 258.75 [M+H]$^+$.

c. Preparation of 1-(3-(morpholinomethyl)pyridin-2-yl)ethan-1-one (4)

To a solution of 4-((2-bromopyridin-3-yl)methyl)morpholine (3) (1.55 g, 6.03 mmol, 1.0 eq) in 18 ml dioxane was added tributyl(1-ethoxyvinyl)tin (2.61 g, 7.24 mmol, 1.2 eq), and PdCl$_2$(PPh$_3$)$_2$ (212 mg, 0.302 mmol, 0.05 eq). The reaction was heated in a microwave reactor for 30 min at 140° C. The crude reaction was diluted in EtOAc, filtered over celite, washed with EtOAc and concentrated to give the crude vinyl ether. A solution of the concentrate dissolved in 10 ml dioxane and 10 ml 2M HCl (aq) was stirred overnight at room temperature. After determining completion by LC/MS the reaction was partitioned in EtOAc and water. The organic was extracted 2× water (mildly acidic from reaction). The combined aqueous was basified with 1M NaOH (aq) and extracted 3× EtOAc. The combined organic was washed 1× brine, dried over sodium sulfate, filtered and concentrated. Purification by silica gel chromatography (10%→25%→50% EtOAc/Hex) afforded 1-(3-(morpholinomethyl)pyridin-2-yl)ethan-1-one (4) (1.1 g, 83% yield, 95% purity by LC/MS) as a pale orange oil after concentration. MS: 220.65 [M+H]$^+$.

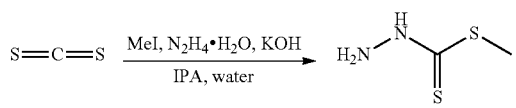

d. Preparation of Methyl Hydrazinecarbodithioate (8)

To a solution of KOH (5.6 g, 100 mmol, 1 eq) in 10 ml water was added 10 ml isopropanol. The reaction was cooled to 0° C. and all subsequent additions were performed at this temperature. Hydrazine hydrate (6.15 ml, 100 mmol, 1 eq) was added and the solution was stirred for 30 min. After dropwise addition of carbon disulfide (6.04 ml, 100 mmol, 1 eq) over 30 min, the reaction was stirred for 1 hour. Methyl iodide was added dropwise over 30 min and the reaction was allowed to stir for 1 hour. The white solid formed in the reaction was filtered and washed with ice water. The solid was dried under vacuum, dissolved in dichloromethane, dried over sodium sulfate, filtered and concentrated. The concentrate was recrystallized from dichloromethane and filtered to give methyl hydrazinecarbodithioate (8) (5.25 g, 43% yield) as a white crystalline solid.

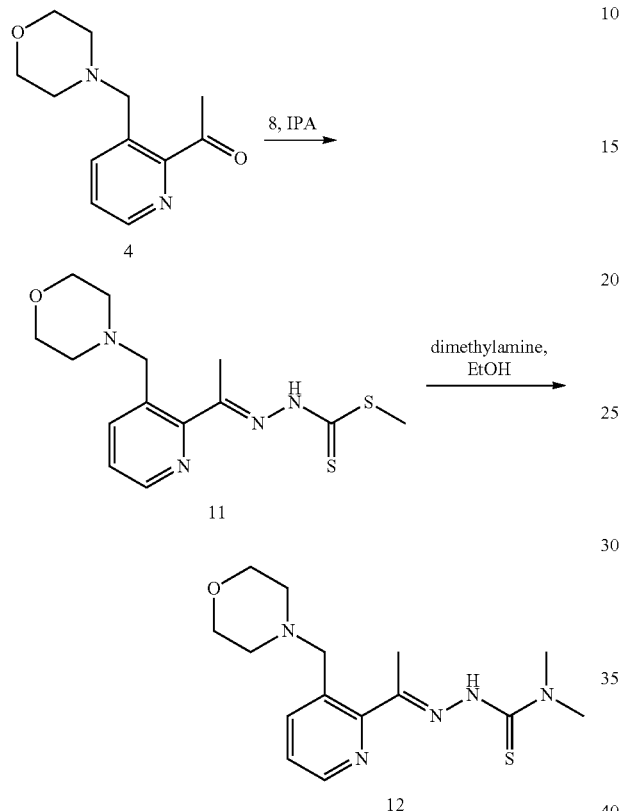

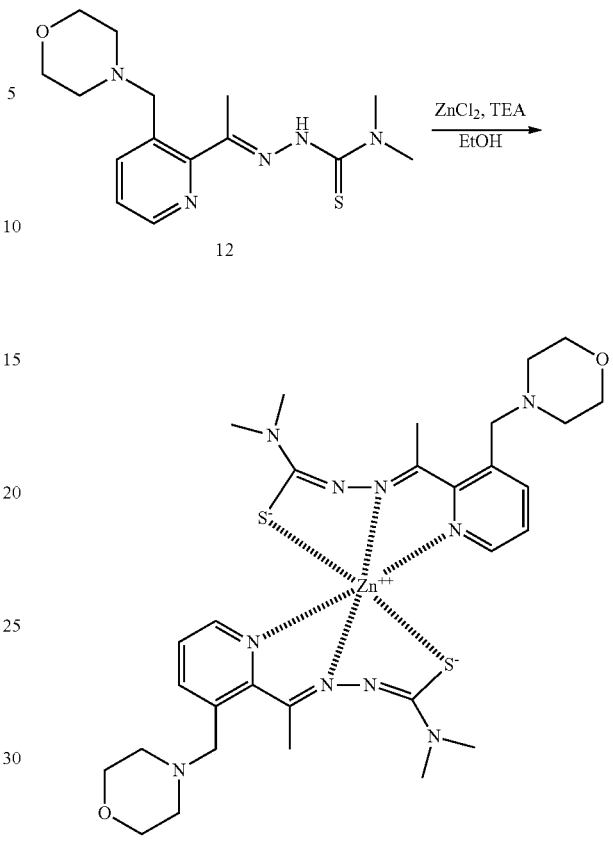

ZN-7 e. Preparation of Methyl (E)-2-(1-(3-(morpholinomethyl)pyridin-2-yl)ethylidene)hydrazine-1-carbodithioate (11)

Following the procedure for the synthesis of (9), methyl (E)-2-(1-(3-(morpholinomethyl)pyridin-2-yl)ethylidene)hydrazine-1-carbodithioate (11) (1.42 g, 99% purity by LC/MS) was synthesized from (4) (1.1 g, 5 mmol) and isolated as a light yellow solid. MS: 324.70 [M+H]$^+$.

f. Preparation of (E)-N,N-dimethyl-2-(1-(3-(morpholinomethyl)pyridin-2-yl)ethylidene)hydrazine-1-carbothioamide (12)

Following the procedure for the synthesis of (10), (E)-N, N-dimethyl-2-(1-(3-(morpholinomethyl)pyridin-2-yl)ethylidene)hydrazine-1-carbothioamide (12) (920 mg, 100% purity by LC/MS) was synthesized from (11) (1.42 g, 4.38 mmol) as a yellow solid. $^1$H NMR (400 MHz, DMSO-d6) δ 9.48 (s, 1H), 8.48 (s, 1H), 7.90 (d, J=7.7 Hz, 1H), 7.36 (s, 1H), 3.91 (s, 2H), 3.55 (s, 5H), 3.32 (s, 6H), 2.33 (s, 6H). MS: 321.70 [M+H]$^+$.

g. Preparation of Zn[(E)-N,N-dimethyl-2-(1-(3-(morpholinomethyl)pyridin-2-yl)ethylidene)hydrazine-1-carbothioamide]$_2$ (ZN-7)

To a suspension of (E)-N,N-dimethyl-2-(1-(3-(morpholinomethyl)pyridin-2-yl)ethylidene)hydrazine-1-carbothioamide (12) (915 mg, 2.85 mmol, 1 eq) and zinc chloride (195 mg, 1.43 mmol, 0.5 eq) in 30 ml EtOH was added 2 ml triethylamine. The mixture was refluxed for 4 hours followed by overnight stirring at room temperature. The precipitated solid was sonicated, filtered, washed with cold EtOH and dried under vacuum to give Zn[(E)-N,N-dimethyl-2-(1-(3-(morpholinomethyl)pyridin-2-yl)ethylidene) hydrazine-1-carbothioamide]$_2$ (ZN-7) (948 mg, 94% yield) as a yellow solid in high purity as determined by NMR. $^1$H NMR (400 MHz, DMSO-d6) δ 7.74 (dd, J=7.7, 1.7 Hz, 1H), 7.69 (dd, J=4.9, 1.7 Hz, 1H), 7.18 (dd, J=7.7, 4.9 Hz, 1H), 3.80-3.58 (m, 2H), 3.54 (t, J=4.7 Hz, 4H), 3.21 (s, 6H), 2.73 (s, 3H), 2.28 (d, J=6.5 Hz, 4H). MS: 704.80, 706.35, 707.40, 709.00 [M+H]$^+$.

Example 2 Synthesis of Zn[(E)-2-(1-(3-((2-methoxyethoxy)methyl)pyridin-2-yl)ethylidene)-N,N-dimethylhydrazine-1-carbothioamide]$_2$ (ZN-6)

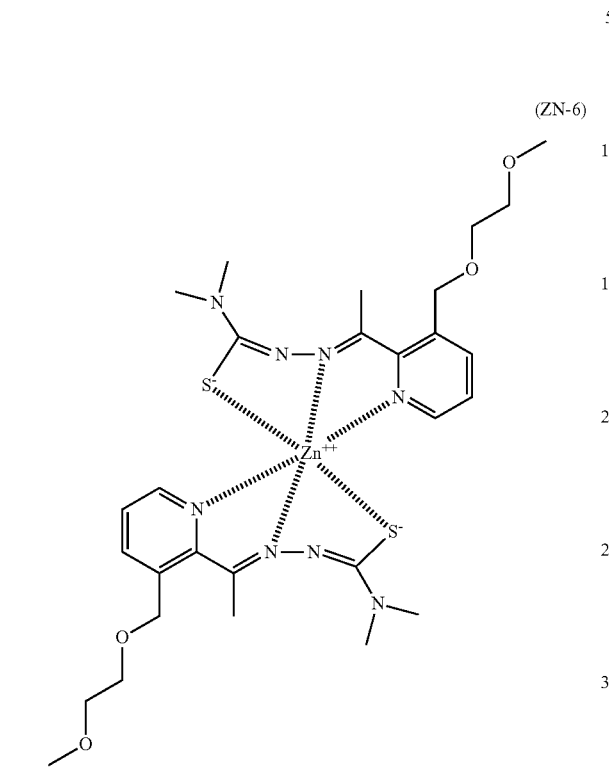

(ZN-6)

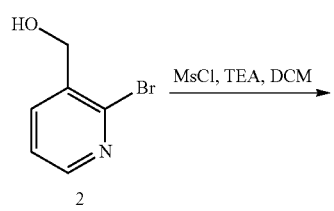

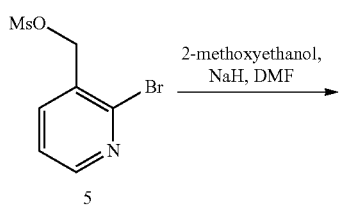

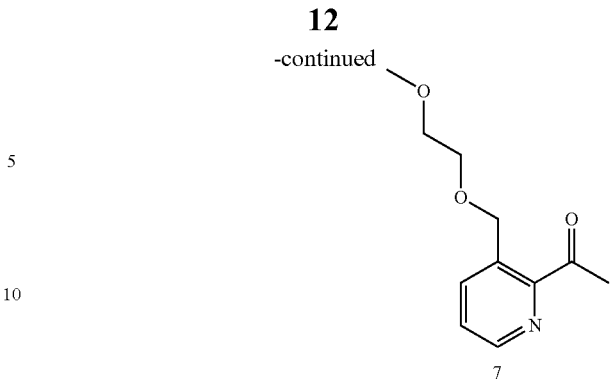

a. Preparation of 2-bromo-3-((2-methoxyethoxy)methyl)pyridine (6)

To a solution of (2-bromopyridin-3-yl)methanol (2) (2.0 g, 10.6 mmol, 1 eq) in 80 ml DCM at 0° C. was added sequentially triethylamine (2.2 ml, 15.9 mmol, 1.5 eq) and methanesulfonyl chloride (820 ul, 10.6 mmol, 1 eq). After stirring for 5 min, the reaction was determined complete by TLC and partitioned in DCM, water. The organic was washed 2× water, 1× brine, dried over sodium sulfate and concentrated to afford crude (2-bromopyridin-3-yl)methyl methanesulfonate (5) in quantitative yield. MS: 265.44, 267.45 [M+H]$^+$. The crude mesylate was dissolved in 60 ml DMF and cooled to 0° C. To this solution was added 2-methoxyethanol (2.51 ml, 31.8 mmol, 3 eq) followed by sodium hydride (60% dispersion, 1.27 g, 31.8 mmol, 3 eq). The reaction was allowed to warm to room temperature and stirred for 15 min. After determining complete by LC/MS, the reaction was quenched with water and concentrated under reduced pressure to remove the majority of the DMF. The concentrate was partitioned in EtOAc/water, washed 2× water, 1× brine, dried over sodium sulfate, filtered and concentrated. After purification by silica gel chromatography (20% EtOAc/Hex), 2-bromo-3-((2-methoxyethoxy)methyl)pyridine (6) (2.25 g, 84% yield over 2 steps, 98% purity by LC/MS) was isolated as a pale yellow oil. MS: 245.55, 247.55 [M+H]$^+$.

b. Preparation of 1-(3-((2-methoxyethoxy)methyl)pyridin-2-yl)ethan-1-one (7)

Following the procedure outlined for the synthesis of (4), 1-(3-((2-methoxyethoxy)methyl)pyridin-2-yl)ethan-1-one (7) (1.52 g, 67% yield over 2 steps, 100% purity by LC/MS) was synthesized from 2-bromo-3-((2-methoxyethoxy)methyl)pyridine (6) and isolated as a yellow oil after purification by silica gel chromatography (10%→25%→50% EtOAc/Hex). MS: 209.75 [M+H]$^+$.

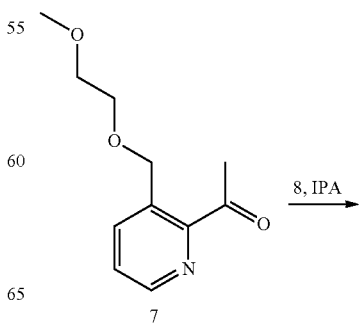

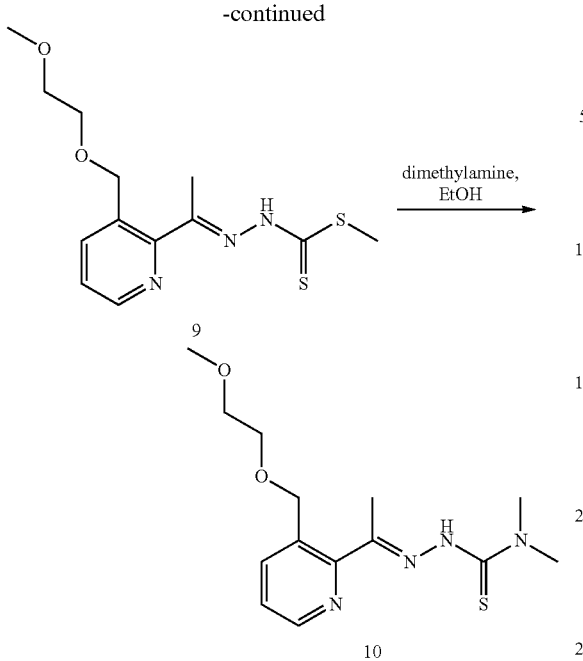

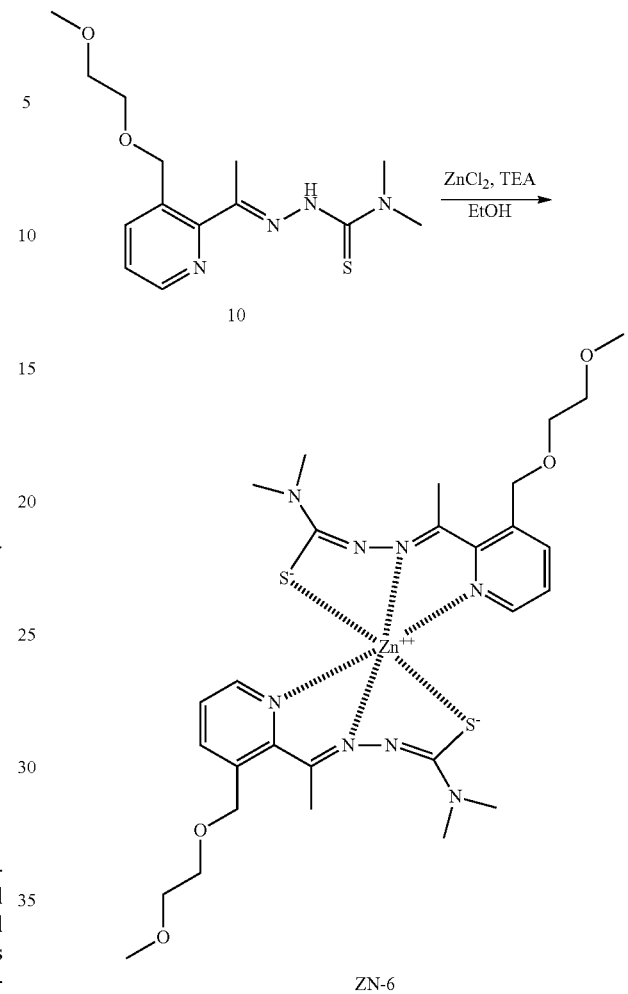

ZN-6 c. Preparation of Methyl (E)-2-(1-(3-((2-methoxyethoxy)methyl)pyridin-2-yl)ethylidene)hydrazine-1-carbodithioate (9)

A solution of 1-(3-((2-methoxyethoxy)methyl)pyridin-2-yl)ethan-1-one (7) (1.25 g, 6 mmol, 1 eq) and methyl hydrazinecarbodithioate (8) (738 mg, 6 mmol, 1 eq) in 15 ml isopropanol was heated overnight at 60° C. The reaction was determined complete by LC/MS and cooled to room temperature. The precipitated solid was filtered, washed with isopropanol and dried under vacuum to give methyl (E)-2-(1-(3-((2-methoxyethoxy)methyl)pyridin-2-yl)ethylidene)hydrazine-1-carbodithioate (9) (1.95 g, quantitative yield, 100% purity by LC/MS as a light yellow solid. MS: 313.70 [M+H]$^+$, MS: 335.85 [M+Na]$_+$.

d. Preparation of (E)-2-(1-(3-((2-methoxyethoxy)methyl)pyridin-2-yl)ethylidene)-N,N-dimethylhydrazine-1-carbothioamide (10)

Methyl (E)-2-(1-(3-((2-methoxyethoxy)methyl)pyridin-2-yl)ethylidene)hydrazine-1-carbodithioate (9) (1.95 g, 6.22 mmol) was dissolved in 10 ml EtOH, 5 ml dimethylamine (40% in water) and heated overnight at 60° C. in a sealed reaction vessel. The reaction was determined complete by LC/MS and cooled to room temperature. The crude reaction was concentrated and purified by silica gel chromatography (2%→4 5%→10% MeOH/DCM). Product containing fractions were concentrated and recrystallized from EtOH to afford (F)-2-(1-(3-((2-methoxyethoxy)methyl)pyridin-2-yl)ethylidene)-N,N-dimethylhydrazine-1-carbothioamide (10) (1.01 g, 99% purity) as a light yellow solid. $^1$H NMR (400 MHz, DMSO-d6) δ 9.54 (s, 1H), 8.52 (dd, J=4.7, 1.7 Hz, 1H), 7.99 (ddt, J=7.9, 1.8, 0.9 Hz, 1H), 7.41 (dd, J=7.9, 4.7 Hz, 1H), 4.98 (s, 2H), 3.66-3.60 (m, 2H), 3.57-3.52 (m, 2H), 3.32 (s, 6H), 3.27 (s, 3H), 2.39 (s, 3H). MS: 310.75 [M+H]$^+$, MS: 332.95 [M+Na]$^+$.

e. Preparation of Zn[(E)-2-(1-(3-((2-methoxyethoxy)methyl)pyridin-2-yl)ethylidene)-N,N-dimethylhydrazine-1-carbothioamide]2 (ZN-6)

(E)-2-(1-(3-((2-methoxyethoxy)methyl)pyridin-2-yl)ethylidene)-N,N-dimethylhydrazine-1-carbothioamide (10) (1.01 g, 3.25 mmol, 1 eq) and zinc chloride (222 mg, 1.63 mmol, 0.5 eq) were taken up in 30 ml ethanol. To this suspension was added 2 ml TEA. The reaction was stirred for 4 hours at reflux followed by overnight at room temperature. The mixture was sonicated, filtered, washed with cold ethanol and dried under vacuum. The filtrate was concentrated and taken up in 5 ml ethanol. Following sonication, a second crop of product was filtered, washed with cold ethanol and dried under vacuum. The two crops of solid were combined to give Zn[(IF)-2-(I-(3-((2-methoxyethoxy)methyl)pyridin-2-yl)ethylidene)-N,N-dimethylhydrazine-1-carbothioamide]$_2$ (ZN-6) (1.004 g, 90% yield) in high purity as determined by NMR $^1$H NMR (400 MHz, DMSO-d6) S 7.85 (dd, J=7.8, 1.7 Hz, 1H), 7.69 (dd, J=4.9, 1.7 Hz, 1H), 7.25 (dd, J=7.7, 4.8 Hz, 1H), 4.73 (s, 2H), 3.64-3.58 (m, 2H), 3.52-3.46 (m, 2H), 3.25 (s, 3H), 3.21 (s, 6H), 2.68 (s, 3H). MS: 682.90, 684.75, 686.95 [M+H]$^+$.

Example 3 Synthesis of Zn[(E)-2-(1-(4-((2-methoxyethoxy)methyl)pyridin-2-yl)ethylidene)-N,N-dimethylhydrazine-1-carbothioamide]2 (ZN-12)

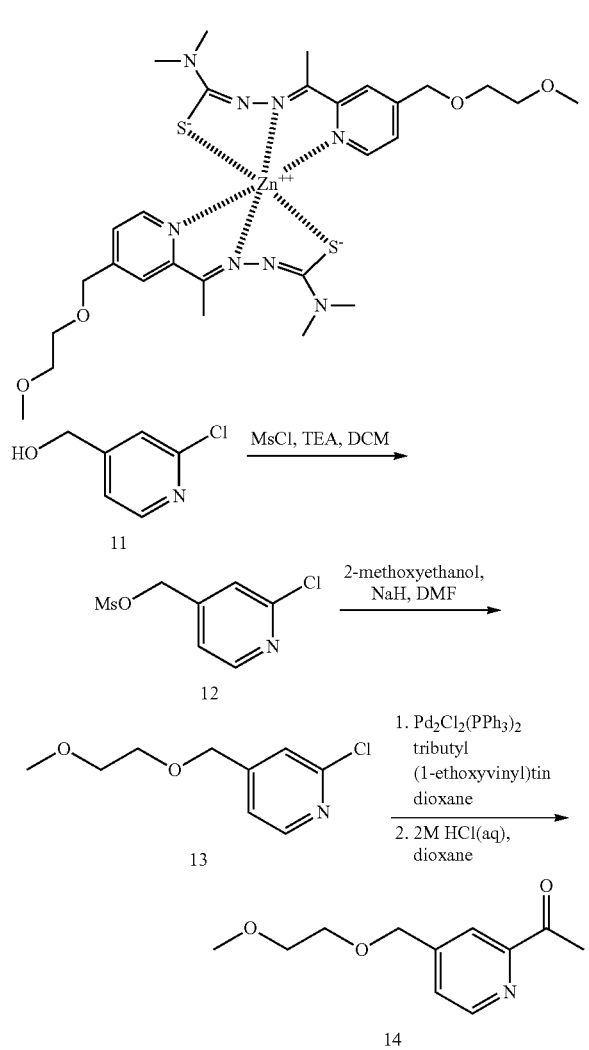

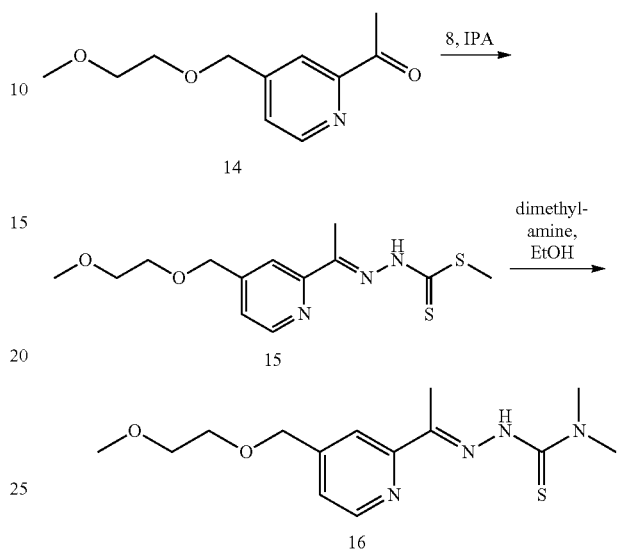

a. Preparation of 2-chloro-4-((2-methoxyethoxy)methyl)pyridine (13)

Following the procedure outlined for the synthesis of (5), (2-chloropyridin-4-yl)methyl methanesulfonate (12) (quantitative yield) was synthesized from (2-chloropyridin-4-yl)methanol (11) (1.44 g, 10.0 mmol) and isolated as a tan solid after work-up and concentration. MS: 222.85 [M+H]+. Following the procedure outlined for the synthesis of (6) 2-chloro-4-((2-methoxyethoxy)methyl)pyridine (13) (413 mg, 21% yield over 2 steps, 89% purity by LC/MS) was isolated as a light yellow oil. MS: 201.85 [M+H]+.

b. Preparation of 1-(4-((2-methoxyethoxy)methyl)pyridin-2-yl)ethan-1-one (14)

Following the procedure outlined for the synthesis of (4), 1-(4-((2-methoxyethoxy)methyl)pyridin-2-yl)ethan-1-one (14) (260 mg, 62% yield over 2 steps, 96% purity by LC/MS) was synthesized from 2-chloro-4-((2-methoxyethoxy)methyl)pyridine (13) (405 mg, 2.0 mmol) and isolated as a light yellow oil after purification by silica gel chromatography (10%→25%→50% EtOAc/Hex). MS: 209.95 [M+H]+.

c. Preparation of Methyl (E)-2-(1-(4-((2-methoxyethoxy)methyl)pyridin-2-yl)ethylidene)hydrazine-1-carbodithioate (15)

Following the procedure for the synthesis of (9), methyl (E)-2-(1-(4-((2-methoxyethoxy)methyl)pyridin-2-yl)ethylidene)hydrazine-1-carbodithioate (15) (268 mg, 98% purity by LC/MS) was synthesized from (14) (209 mg, 1.0 mmol) and isolated as a tan solid. MS: 314.30 [M+H]+.

d. Preparation of (E)-2-(1-(4-((2-methoxyethoxy)methyl)pyridin-2-yl)ethylidene)-N,N-dimethylhydrazine-1-carbothioamide (16)

Following the procedure for the synthesis of (10), (E)-2-(1-(4-((2-methoxyethoxy)methyl)pyridin-2-yl)ethylidene)-N,N-dimethylhydrazine-1-carbothioamide (16) (119 mg, 98% purity by LC/MS) was synthesized from (11) (135 mg, 0.431 mmol) as a yellow solid after recrystallization from isopropanol. $^1$H NMR (500 MHz, DMSO-dh) δ 9.61 (s, 1H), 8.75-8.54 (m, 1H), 7.99-7.72 (m, 1H), 7.5-7.31 (m, 1H), 4.71-4.56 (m, 2H), 3.70-3.58 (m, 2H), 3.58-3.47 (m, 2H), 3.38-3.24 (m, 9H), 2.63 (m, J=2.8 Hz, 1H), 2.38 (m, J=6.8 Hz, 2H). Note: Peaks have complex splitting from multiple conformational isomers. MS: 311.05 [M+H]+.

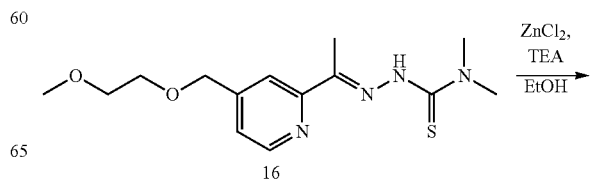

-continued

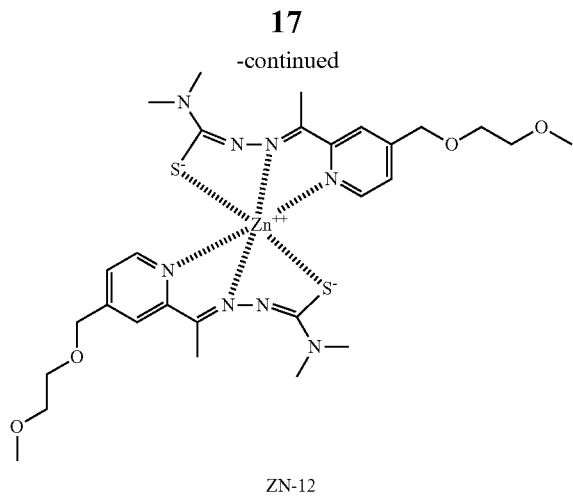

ZN-12 e. Preparation of Zn[(E)-2-(1-(4-((2-methoxy-ethoxy)methyl)pyridin-2-yl)ethylidene)-N,N-dimethylhydrazine-1-carbothioamide]$_2$ (ZN-12)

Following the procedure for the synthesis of (ZN-6), the title compound (ZN-12) (91.8 mg) was synthesized from (E)-2-(I-(4-((2-methoxyethoxy)methyl)pyridin-2-yl)ethylidene)-N,N-dimethylhydrazine-1-carbothioamide (16) (111 mg, 0.358 mmol) and isolated as a yellow/orange solid. $^1$H NMR (500 MHz, DMSO-d$_6$) δ 7.69 (dd, J=5.2, 0.7 Hz, 1H), 7.66 (dt, J=1.5, 0.7 Hz, 1H), 7.17 (ddt, J=5.2, 1.4, 0.7 Hz, 1H), 4.54 (s, 2H), 3.63-3.54 (m, 2H), 3.51-3.45 (m, 2H), 3.24 (s, 3H), 3.22 (s, 6H), 2.57 (s, 3H).

Example 4 Solubility of Zinc Complexes

Results of solubility measurements for zinc complexes (ZN-6) and (ZN-7) are shown in the following Table.

| Complex | DMSO | EtOH | 50% EtOH 50% H$_2$O | 10% EtOH, 10% captisol, 80% water | 5% EtOH, 4% Tween80, 4% Kolliphor, 87% water |
|---|---|---|---|---|---|
| ZN-6 | >10 mg/ml | >10 mg/ml | >5 mg/mL | 1 mg/ml | 1 mg/ml |
| ZN-7 | >5 mg/ml | 1-2 mg/ml | ND | ND | ND |

ND (not determined)

Example 5 Cell Growth Inhibition Assay

Cell growth inhibition assay using human tumor cell lines with different p53 status (wildtype, null, p53-R175H or other zinc binding deficient mutants) were employed to determine if a test compound functions as a zinc metallochaperone to restore wildtype p53 functions. The cell growth inhibition assay was performed by Calcein AM assay (Trevigen). Five thousand cells per well were cultured in 96-well plate to reach the 50% confluence on the second day when treated with serial dilutions of the compounds. Growth was measured by Calcein AM assay (Trevigen) and Victor Plate reader instrument (PerkinElmer) after incubation for 3 days. EC$_{50}$s were compared to ZN-1 for efficacy. Results are shown in the following table.

| | EC$_{50}$s of ZN-6, ZN-7 and ZN-12, compared with ZN-1 | | |
|---|---|---|---|
| | EC$_{50}$ (nM) | Fold (compound/ZN-1) | Fold (ZN-1/compound) |
| ZN-1 | 2.69 | 1.0 | 1.0 |
| ZN-6 | 5.41 | 2.0 | 0.5 |
| ZN-7 | 8.36 | 3.1 | 0.3 |
| ZN-12 | 2.52 | 0.9 | 1.1 |

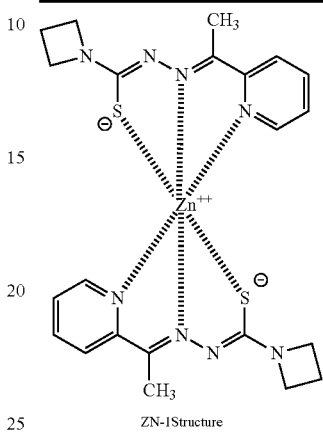

ZN-1Structure

Example 6 Mutant p53 Refolding Assay

An immunofluorescent staining using p53 conformation specific antibodies was used to determine if a test compound could induce the mutant p53 protein refolding to a wildtype conformation. The p53-R175H cells (e.g. TOV 112D) cultured in DMEM+10% FBS were treated with a test compound for 6 hours, then fixed and stained with the antibodies PAB1620 (recognizing WT conformation) and PAB240 (recognizing misfolded/unfolded conformation) respectively. ZN-6 was found to change the mutant p53-R175H protein from mutant conformation to WT conformation, like ZMC1 and its complex ZN-1 (data not shown).

Example 7 Mutant p53 Transcriptional Reactivation Assay by Gene Expression Regulation Measurement p53 is a transcription factor. The reactivation of mutant p53 can be detected by regulation of the p53 target genes using quantitative reverse transcription PCR (qRT-PCR). The p53-R175H cells were treated with the compound for 6 hours and 24 hours followed by qRT-PCR to analyze the gene expression regulation. The two p53 target genes in this assay were PUMA and GDF15. For ZN-6, the expression levels were induced for 18-fold and 53-fold respectively (in parental cells). To double check the p53 dependence of the effect, the same assay applied to the p53 knockout cell line (KO, done by CRISPR-cas9 technology) and the p53 transient knockdown cells (KD, using siRNA knockdown). The PUMA induction was only 2× and 5× and GDF15 induction was only 1× and 5× in KO and KD cells, respectively (See FIG. 1). This is strongly indicated that the ZN-6 reactivation function is p53 dependent.

Example 8 Colonogenic Assay for Long Term Cell Killing

Figure 2:
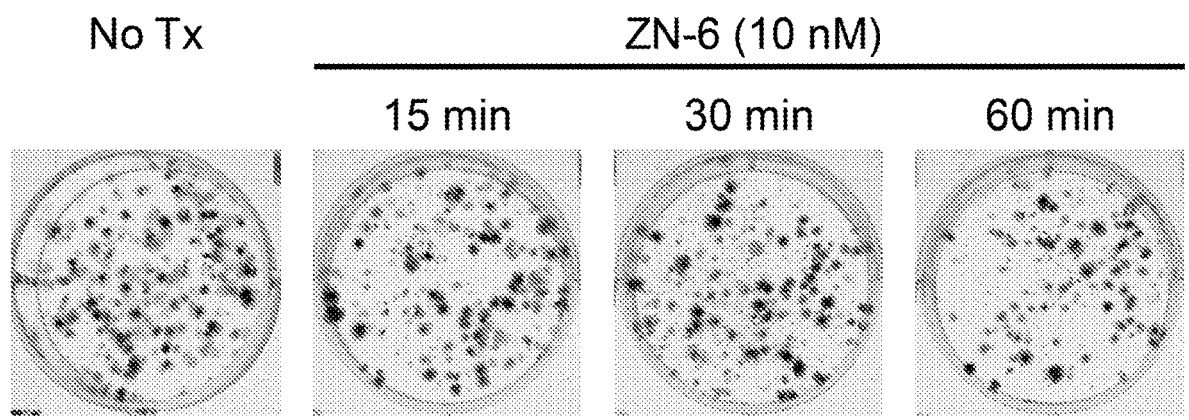
FIG. 2 shows data from Example 8.

Cell growth inhibition for 3 days is an effect for a short term treatment. A colonogenic assay was used for the long term cell killing effect. One thousand cells were seeded in each well in 6-well plates. On the second day the cells were exposed with the dilutions of the compound for up to 60 minutes. After that the compound was washed away and the cells were refed with fresh medium without the compound. The colonies were visualized by crystal violet staining after 14-day incubation. ZN-6 (10 nM) showed effect as early as 15 minutes (See FIG. 2), like ZMC1 and ZN-1.

Example 9 In Vivo Assays

Mice are housed and treated according to guidelines and all the mouse experiments are done with the approval of Institutional Animal Care and Use Committee (IACUC). For Maximum tolerated dose assays, 8-12 week old mice (5 mice per dose) are administered by intraperitoneal injection (IP) daily with various doses for 14 days and health, behavior and body weight are monitored. Human cancer cell lines and mouse tumor cell lines are implanted into the nude mice (NCR nu/nu) for Xenograft tumor assays. Tumor dimensions are measured every other day and their volumes are calculated by length (L) and width (W) using the formula: volume=L×W²×π/6. Tumors over 50 mm³ are treated by daily administration of a test compound by intravenous injection (IV) or IP. Genetically engineered transgenic KPC mice (Pdx1-CRE; KRas$^{G12D/+}$; p53$^{R172H/+}$ and Pdx1-CRE; KRas$^{G12D/+}$; p53$^{R70H/+}$) are administered a test compound by IP daily. The survival and the tumor growth rate represent the efficacy of a test compound. The endogenous tumor growth is monitored with ultrasound by VisualSonics Vevo 3100.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A complex comprising $Zn^{2+}$ and a compound of formula (I):

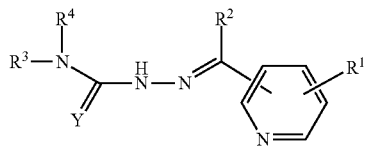
(I)

or a deuterated analog thereof, or an ion or poly-ion thereof, or a salt of said complex, wherein:
$R^1$ is morpholinomethyl, 2-morpholinoethyl, or $(C_1-C_6)$ alkyl that is substituted with $(C_1-C_6)$alkoxy that is substituted with one or more groups independently selected from $(C_1-C_6)$alkoxy, halo, cyano, $(C_3-C_6)$cycloalkyl, $(C_2-C_6)$alkanoyloxy, $(C_2-C_6)$alkoxycarbonyl, and $-N(R^a)_2$;

$R^2$ is selected from the group consisting of H, phenyl, heteroaryl, $(C_1-C_6)$alkyl, $(C_2-C_6)$alkenyl, $(C_2-C_6)$alkynyl, and $(C_3-C_6)$cycloalkyl, wherein any phenyl, heteroaryl, $(C_1-C_6)$alkyl, $(C_2-C_6)$alkenyl, $(C_2-C_6)$alkynyl, and $(C_3-C_6)$cycloalkyl is optionally substituted with one or more groups independently selected from halo, $-N(R^b)_2$, $(C_3-C_6)$cycloalkyl, $(C_1-C_6)$alkoxy, $(C_2-C_6)$alkanoyloxy, $(C_2-C_6)$alkoxycarbonyl, $(C_2-C_6)$alkylaminocarbonyl, and $(C_2-C_6)$alkanoylamino;

$R^3$ and $R^4$ are each independently selected from H, $(C_1-C_6)$alkyl, piperidinyl, or piperazinyl, which piperidinyl or piperazinyl is optionally substituted with pyridyl; or $R^3$ and each $R^4$ taken together with the nitrogen to which they are attached form a 3, 4, 5, 6, 7, 8, or 9 membered ring that is optionally substituted with one or more groups independently selected from the group consisting of halo;

Y is S, O, or Se;

each $R^a$ is independently selected from the group consisting of H, $(C_1-C_6)$alkyl, $(C_3-C_6)$alkenyl, $(C_3-C_6)$alkynyl, $(C_3-C_6)$cycloalkyl, $(C_1-C_6)$alkanoyl, $(C_1-C_6)$alkylaminocarbonyl and $(C_1-C_6)$alkoxycarbonyl, wherein any $(C_1-C_6)$alkyl, $(C_3-C_6)$alkenyl, $(C_3-C_6)$alkynyl, $(C_3-C_6)$cycloalkyl, $(C_1-C_6)$alkanoyl, $(C_1-C_6)$alkoxycarbonyl, and $(C_1-C_6)$alkylaminocarbonyl, is optionally substituted with one or more groups independently selected from halo, $(C_3-C_6)$cycloalkyl, and $(C_1-C_6)$alkoxy; or two $R^a$ taken together with the nitrogen to which they are attached form an azetidino, pyrrolidino, piperidino, or morpholino ring; and each $R^b$ is independently selected from the group consisting of H, $(C_1-C_6)$alkyl, $(C_3-C_6)$alkenyl, $(C_3-C_6)$alkynyl, $(C_3-C_6)$cycloalkyl, $(C_1-C_6)$alkanoyl, $(C_1-C_6)$alkylaminocarbonyl and $(C_1-C_6)$alkoxycarbonyl, wherein any $(C_1-C_6)$alkyl, $(C_3-C_6)$alkenyl, $(C_3-C_6)$alkynyl, $(C_3-C_6)$cycloalkyl, $(C_1-C_6)$alkanoyl, $(C_1-C_6)$alkoxycarbonyl, and $(C_1-C_6)$alkylaminocarbonyl, is optionally substituted with one or more groups independently selected from halo, $(C_3-C_6)$cycloalkyl, and $(C_1-C_6)$alkoxy; or two $R^a$ taken together with the nitrogen to which they are attached form an azetidino, pyrrolidino, piperidino, or morpholino ring.

2. The complex of claim 1, which comprises a compound of formula (Ia):

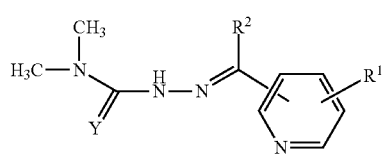
(Ia)

or a deuterated analog thereof, or an ion or poly-ion thereof, or a salt of said complex.

3. The complex of claim 1, which comprises a compound of formula (Ib):

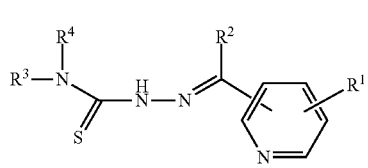

or a deuterated analog thereof, or an ion or poly-ion thereof, or a salt of said complex.

4. The complex of claim 1, which comprises a compound of formula (Ih):

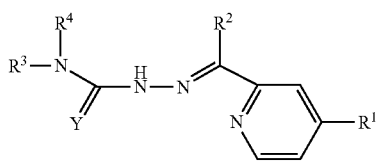

or a deuterated analog thereof, or an ion or poly-ion thereof, or a salt of said complex.

5. The complex of claim 1, which comprises a compound of formula (Im):

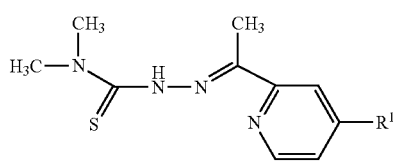

or a deuterated analog thereof, or an ion or poly-ion thereof, or a salt of said complex.

6. The complex of claim 1, wherein $R^1$ is morpholinomethyl.

7. The complex of claim 1, wherein $R^1$ is $(C_1-C_6)$alkyl that is substituted with $(C_1-C_6)$alkoxy that is substituted with one or more groups independently selected from $(C_1-C_6)$alkoxy, halo, cyano, $(C_3-C_6)$cycloalkyl, $(C_2-C_6)$alkanoyloxy, $(C_2-C_6)$alkoxycarbonyl, and $—N(R^a)_2$.

8. The complex of claim 1, wherein $R^1$ is $(C_1-C_6)$alkyl that is substituted with $(C_1-C_6)$alkoxy that is substituted with $(C_1-C_6)$alkoxy.

9. The complex of claim 1, wherein $R^1$ is methyl that is substituted with $(C_1-C_6)$alkoxy that is substituted with $(C_1-C_6)$alkoxy.

10. The complex of claim 1, wherein $R^1$ is methyl that is substituted with ethoxy that is substituted with $(C_1-C_6)$alkoxy.

11. The complex of claim 1, wherein the compound and the $Zn^{2+}$ are present in a ratio of about 2:1.

12. The complex of claim 1, which is a complex of formula:

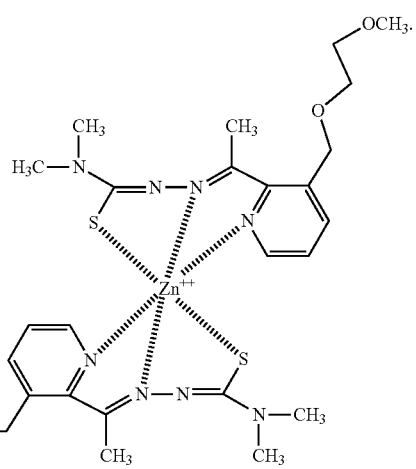

13. The complex of claim 1, which is a complex of formula:

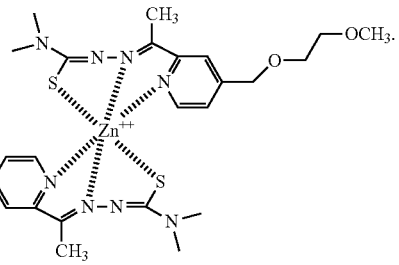

14. The complex of claim 1, wherein the compound of formula (I) is selected from the group consisting of:

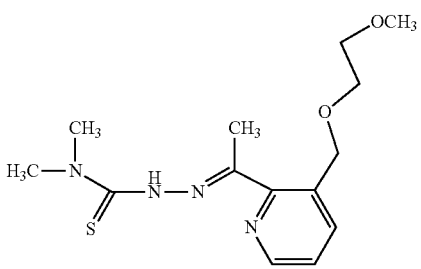

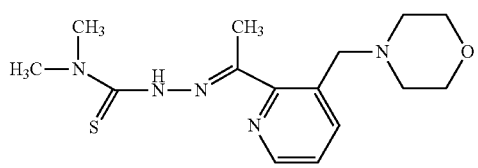

and

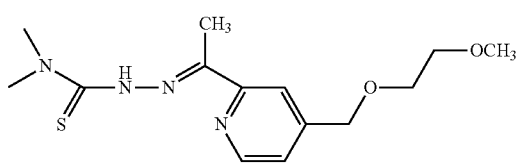 [SMILES: COCCOCc1ccnc(/C(C)=N/NC(=S)N(C)C)c1]

or an ion or poly-ion thereof, or a salt of said complex.

15. A pharmaceutical composition, comprising a complex of claim 1 or a solvate thereof, and a pharmaceutically acceptable carrier.

16. A method of treating cancer in an animal comprising administering a complex of claim 1 to the animal.

17. The method of claim 16, further comprising administering a chemotherapeutic agent to the animal.

18. The method of claim 17 wherein the chemotherapeutic agent is selected from the group consisting of: Actinomycin, All-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vemurafenib, Vinblastine, Vincristine, Vindesine, and Vinorelbine.

19. A compound selected from the group consisting of:

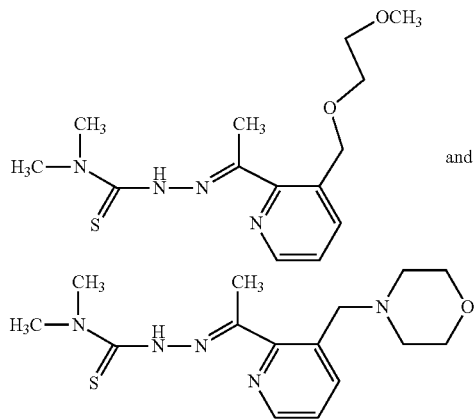

or an ion or poly-ion thereof, or a salt thereof.

* * * * *